US011155854B2

(12) United States Patent
Vauterin et al.

(10) Patent No.: US 11,155,854 B2
(45) Date of Patent: Oct. 26, 2021

(54) METHOD AND SYSTEM FOR ESTIMATING A GENDER OF A FOETUS OF A PREGNANT FEMALE

(71) Applicant: AGILENT TECHNOLOGIES, INC., Santa Clara, CA (US)

(72) Inventors: Paul Vauterin, Niel (BE); Michaël Vyverman, Niel (BE); Joachim De Schrijver, Niel (BE)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 296 days.

(21) Appl. No.: 15/737,093

(22) PCT Filed: Jul. 13, 2016

(86) PCT No.: PCT/EP2016/066653
§ 371 (c)(1),
(2) Date: Dec. 15, 2017

(87) PCT Pub. No.: WO2017/012954
PCT Pub. Date: Jan. 26, 2017

(65) Prior Publication Data
US 2018/0171390 A1 Jun. 21, 2018

(30) Foreign Application Priority Data
Jul. 17, 2015 (BE) .................................. 2015/5464

(51) Int. Cl.
*C12Q 1/6879* (2018.01)
*G16H 50/20* (2018.01)
(Continued)

(52) U.S. Cl.
CPC .......... *C12Q 1/6809* (2013.01); *C12Q 1/686* (2013.01); *C12Q 1/6879* (2013.01);
(Continued)

(58) Field of Classification Search
None
See application file for complete search history.

(56) References Cited

U.S. PATENT DOCUMENTS

2013/0275103 A1 10/2013 Struble et al.
2014/0099642 A1 4/2014 Jiang et al.

FOREIGN PATENT DOCUMENTS

WO WO 2011/091063 A1 7/2011
WO WO 2013/057568 A1 4/2013
(Continued)

OTHER PUBLICATIONS

Dar, P. et al. American Journal of Obstetrics & Gynecology 211:527. e1-17. Disclosed March and May/Jun. 2014, published Nov. 2014. (Year: 2014).*
(Continued)

*Primary Examiner* — Diana B Johannsen
(74) *Attorney, Agent, or Firm* — Arent Fox LLP (57) ABSTRACT

A method for estimating a gender of a foetus of a pregnant female, said method comprising measuring allele presences ($D_X$) for a first plurality of genetic markers of the X-chromosome and allele presences (DR) for a second plurality of genetic markers of at least one reference chromosome, different from the X and Y chromosome, in a sample of cell-free DNA from a pregnant female; based on said measured allele presences for said first plurality, determining a first fraction thereof which is associated with purely homozygous genetic markers; based on said measured allele presences for said second plurality, determining a second fraction thereof which is associated with purely homozygous genetic markers; and estimating a gender of said foetus based on said first and second fraction.

7 Claims, 9 Drawing Sheets

(51) Int. Cl.
*C12Q 1/6809* (2018.01)
*G16B 20/00* (2019.01)
*G16H 10/40* (2018.01)
*C12Q 1/686* (2018.01)
*G01N 33/68* (2006.01)

(52) U.S. Cl.
CPC ........... *G01N 33/689* (2013.01); *G16B 20/00* (2019.02); *G16H 10/40* (2018.01); *G16H 50/20* (2018.01); *C12Q 2537/16* (2013.01); *C12Q 2537/165* (2013.01); *C12Q 2600/156* (2013.01)

(56) References Cited

FOREIGN PATENT DOCUMENTS

WO    WO 2014/033455 A1    3/2014
WO    WO 2015/035555 A1    3/2015

OTHER PUBLICATIONS

Tungwiwat et al., "Non-invasive fetal sex determination using a conventional nested PCR analysis of fetal DNA in maternal plasma," Clinical Chimica Acta, vol. 334, 2003, pp. 173-177.
Donaghue et al., "Development and targeted application of a rapid QF-PCR test for sex chromosome imbalance," Prenat Diagn vol. 23, 2003, pp. 201-210.
Hill et al., "Non-invasive prenatal determination of fetal sex: translating research into clinical practice," Clin. Genet. vol. 80, 2011; pp. 68-75.
International Search Report issued in international patent application No. PCT/EP2016/066653, dated Sep. 26, 2016 (3 pages).

* cited by examiner

Gender (homozygous): score for gender calling based on monosomy call

METHOD AND SYSTEM FOR ESTIMATING A GENDER OF A FOETUS OF A PREGNANT FEMALE

CROSS REFERENCE TO RELATED APPLICATIONS

This application is a 35 U.S.C. 371 National Phase of PCT Application No. PCT/EP2016/066653 filed Jul. 13, 2016, which claims benefit to BE Application No. 2015/5464 filed Jul. 17, 2015, the disclosure of which is hereby incorporated by reference in its entirety.

FIELD OF INVENTION

The field of the invention relates to estimating a gender of a foetus of a pregnant female. Particular embodiments of the inventions relate to methods, systems, computer programs and computer program products for estimating a gender of a foetus of a pregnant female.

BACKGROUND

WO 2013/057568 in the name of the Applicant discloses prenatal detection methods using non-invasive techniques. In particular, it relates to prenatal diagnosis of a foetal chromosomal aneuploidy by detecting foetal and maternal nucleic acids in a maternal biological sample. More particularly, WO 2013/057568 applies multiplex PCR to amplify selected fractions of the respective chromosomes of maternal and foetal chromosomes. Respective amounts of suspected aneuploid chromosomal regions and reference chromosomes are determined from massive sequencing analysis followed by a statistical analysis to detect a particular aneuploidy.

Although various prenatal detection methods exist, there is a need for an accurate method to estimate the gender of the foetus of a pregnant female.

SUMMARY

The object of embodiments of the invention is to provide a method, system and computer program for estimating the gender of the foetus of a pregnant female.

According to a first aspect of the invention there is provided a method for estimating a gender of a foetus of a pregnant female. The method comprises the step of measuring allele presences for a first plurality of genetic markers of the X-chromosome and allele presences for a second plurality of genetic markers of at least one reference chromosome, different from the X and Y chromosome, in a sample of cell-free DNA from a pregnant female. Each allele presence represents the presence at a genetic marker of at least one of: a reference allele of maternal or foetal origin, and an alternative allele of maternal or foetal origin. For the sake of completeness, it is noted that this does not imply that a distinction can be made between an allele of maternal origin and an allele of foetal origin, but merely that an allele of either origin may be measured. The method further comprises: based on said measured allele presences for said first plurality, determining a first fraction ($F_X$) thereof which is associated with purely homozygous genetic markers, based on said measured allele presences for said second plurality, determining a second fraction ($F_R$) thereof which is associated with purely homozygous genetic markers, and estimating a gender of said foetus based on said first and second fraction. The term "purely homozygous genetic marker" refers to a genetic marker which is both homozygous in the DNA of maternal origin and in the DNA of foetal origin.

Embodiments of the invention are based inter alia on the inventive insight that the expected first fraction on the X-chromosome should be higher in case of a male foetus compared to a female foetus. For a female foetus, this first fraction is expected to be identical to the second fraction obtained from non-X/Y chromosomes. For a male foetus, the first fraction is expected to be higher than the second fraction obtained from the at least one reference chromosome different from the X and Y chromosome. Using this first and second fraction the gender can be accurately estimated.

Estimating the gender of a foetus in accordance with embodiments of the invention allows one to verify the gender as estimated in known estimation methods. This verification will improve the accuracy of an estimation of the gender of a foetus compared to known estimation methods.

In the context of this specification, a 'genetic marker' is a position on the genome that is known to take several possible states over individuals in a population.

In a preferred embodiment the determining of the first fraction comprises: based on said measured allele presences for the first plurality of genetic markers, calculating a corresponding number of allele frequencies for said first plurality; and determining as the first fraction the fraction of said measured allele presences for which the allele frequency is 0 or 1 within a predetermined error margin. A person of skill in the art will understand that the error rate of a sequencing device is an industry standard, and will be well known for a specific manufacturer or instrument, but in a specific embodiment the predetermined error margin is <0.02. Particularly it may be <0.015, <0.01 or <0.005. Similarly the determining of the second fraction may comprise: based on said measured allele presences for the second plurality of genetic markers, calculating a corresponding number of allele frequencies for said second plurality; and determining as the second fraction the fraction of said measured allele presences for which the allele frequency is 0 or 1 within a predetermined error margin. A person of skill in the art will understand that the error rate of a sequencing device is an industry standard, and will be well known for a specific manufacturer or instrument, but in a specific embodiment the predetermined error margin is <0.02. Particularly it may be <0.015, <0.01 or <0.005. Typically the allele presences are plotted as read counts in function of the allele frequency, and the first/second fraction corresponds with the read counts of the variant data points concentrated around allele frequency 0 and around allele frequency 1.

In a preferred embodiment the estimating comprises estimating a first gender estimator using a ratio between the first fraction ($F_X$) and the second fraction ($F_R$). The threshold value for determining the appropriate threshold levels for the ratio to estimate a foetus as male or female should be calculated empirically for each embodiment. A person of skill in the art, using the methods as described herein will be able to calculate said thresholds taking into account the noise levels and the heterozygosity of the samples as described herein. In specific embodiments, where the ratio between $F_X$ and $F_R$ is less than 1.1 the foetus is estimated to be female, particularly the ratio is less than 1.05, less than 1.03, less than 1.01, or less than 1.00. In a particular embodiment where the ratio is approximately 1 the foetus is estimated to be female. In specific embodiments, where the ratio between $F_X$ and $F_R$ is greater than 1.1 the foetus is estimated to be male, particularly the ratio is greater than 1.15, greater than 1.17, greater than 1.18, greater than 1.19, or greater than 1.20. In a particular embodiment the where the ratio is significantly greater than 1 the foetus is estimated to be male.

In a preferred embodiment the measuring and determining steps are performed for a batch comprising a plurality of samples; wherein for each sample of the batch, the first and second fraction are calculated; and wherein the step of estimating the gender is further based on said first and second fraction of each sample. In that way, the accuracy of the estimation result can be further improved.

In a further developed embodiment the step of estimating a gender comprises: determining a first gender estimator ($E_{H1}$) for each sample based on said first and second fraction for said sample; for each sample for which the first gender estimator indicates that the gender of the foetus is female, determining a ratio ($N_{Xi}$) between the measured allele presences for the first plurality and the measured allele presences for the second plurality of genetic markers, and determining statistical distribution parameters of said plurality of ratios for said samples associated with a first gender estimator which indicates that the foetus is female; and using said statistical distribution to determine a second gender estimator. In that way statistical information from a batch of samples is used to improve the gender estimation for a single sample of the batch. In the event that the number of samples in the analysis batch for which the first gender estimator indicates that the gender of the foetus is female, is too small to obtain a reliable estimate of the distribution, this set may be augmented by using samples for which the first gender estimator indicates that the gender of the foetus is male, using a corrective factor.

The step of estimating a gender may then further comprise: determining a combined gender estimator using said first and second gender estimator.

According to another aspect of the invention, there is provided a system for estimating a gender of a foetus of a pregnant female. The system comprises a measurement device, a determination module, and an estimation module. The measurement device is configured for measuring allele presences ($D_X$) for a first plurality of genetic markers of the X-chromosome and allele presences ($D_R$) for a second plurality of genetic markers of at least one reference chromosome, different from the X and Y chromosome, in a sample of cell-free DNA from a pregnant female. This may be any commercially available measurement device suitable for performing such measurements. The determination module is configured for determining a first fraction ($F_X$) of said measured allele presences for said first plurality which is associated with purely homozygous genetic markers, and a second fraction ($F_R$) of said measured allele presences for said second plurality which is associated with purely homozygous genetic markers. The estimation module is configured for estimating a gender of said foetus based on said first and second fraction. In a typical embodiment the determination module and the estimation module are implemented as software.

In a preferred embodiment the determining module is configured for, based on said measured allele presences for the first plurality of genetic markers, calculating a corresponding number of allele frequencies for said first plurality; and for determining as the first fraction the fraction of said measured allele presences for which the allele frequency is 0 or 1 within a predetermined error margin. In a similar manner the determining module may be configured for, based on said measured allele presences for the second plurality of genetic markers, calculating a corresponding number of allele frequencies for said second plurality; and determining as the second fraction the fraction of said measured allele presences for which the allele frequency is 0 or 1 within a predetermined error margin. A person of skill in the art will understand that the error rate of a sequencing device is an industry standard, and will be well known for a specific manufacturer or instrument, but in a specific embodiment the predetermined error margin is <0.02. Particularly it may be <0.015, <0.01 or <0.005.

In a preferred embodiment the estimating module is configured for estimating a first gender estimator using a ratio between the first fraction ($F_X$) and the second fraction ($F_R$). The threshold value for determining the appropriate threshold levels for the ratio to estimate a foetus as male or female should be calculated empirically for each embodiment. A person of skill in the art, using the methods as described herein will be able to calculate said thresholds taking into account the noise levels and the heterozygosity of the samples as described herein. In specific embodiments, where the ratio between $F_X$ and $F_R$ is less than 1.1 the foetus is estimated to be female, particularly the ratio is less than 1.05, less than 1.03, less than 1.01, less than 1.00. In a particular embodiment where the ratio is approximately 1 the foetus is estimated to be female. In specific embodiments, where the ratio between $F_X$ and $F_R$ is greater than 1.1 the foetus is estimated to be male, particularly the ratio is greater than 1.15, greater than 1.17, greater than 1.18, greater than 1.19, or greater than 1.20. In a particular embodiment the where the ratio is significantly greater than 1 the foetus is estimated to be male.

In a preferred embodiment the measuring device and determining module are configured to perform the measuring and determining for a batch comprising a plurality of samples, wherein for each sample of the batch, the first and second fraction are calculated; and wherein the estimating module is configured for estimating the gender based on said first and second fraction of each sample.

In a preferred embodiment the estimating module is configured for estimating a gender in a manner as described in any of the exemplary embodiments of the method.

In a preferred embodiment the measuring module is configured to measure allele presences using at least one of the following: polymerase chain reaction (PCR), ligase chain reaction, nucleic acid sequence based amplification (NASBA), and branched DNA methods; and preferably PCR.

In exemplary embodiments of the invention, the measuring of allele presences may comprise measuring of SNP allele presences and/or measuring allele presences for short insertions and/or deletions.

Preferred embodiments of the method and system of the invention are disclosed in the appended dependent claims.

According to a further aspect of the invention, there is provided a computer program comprising computer-executable instructions to perform, when the program is run on a computer, one or more steps, and in particular the estimating step of embodiments of the method disclosed above.

According to a further aspect of the invention, there is provided a computer device or other hardware device programmed to perform one or more steps, and in particular the estimating step of any one of the embodiments of the method disclosed above. According to another aspect there is provided a data storage device encoding a program in machine-readable and machine-executable form to perform one or more steps of any one of the embodiments of the method disclosed above. The reference to computer-executable instructions/form has to be construed such that it comprises both directly executable machine code, code that must be compiled to be executed, and code that is interpreted instead of executed per se.

BRIEF DESCRIPTION OF THE FIGURES

The accompanying drawings are used to illustrate presently preferred non-limiting exemplary embodiments of a method and system of the present invention. The above and other advantages of the features and objects of the invention will become more apparent and the invention will be better understood from the following detailed description when read in conjunction with the accompanying drawings, in which.

DETAILED DESCRIPTION OF EXEMPLARY EMBODIMENTS

In a Non-Invasive Prenatal Test (NIPT), known in the prior art, cell free DNA (cfDNA) in a maternal serum or plasma sample of a pregnant female is sequenced in order to screen for the presence of chromosomal aneuploidies in the foetus, such as trisomy of chromosome 21.

According to exemplary embodiments of the invention, there is provided a method to estimate the gender of the foetus.

In a typical embodiment, a maternal serum or plasma sample is derived from the maternal blood. This may be a small amount of serum or plasma, e.g. 1 to 20 ml. Depending on the desired accuracy it may be preferred to use larger volumes. The preparation of the serum or plasma from the maternal blood sample may be carried out using standard techniques. Suitable techniques include centrifugation and/or matrix based techniques. In possible embodiments, a sequence-based enrichment method may be used on the maternal serum or plasma to specifically enrich for foetal nucleic acid sequences.

Embodiments of the method of the invention may be carried out for a sample containing foetal DNA at a foetal fraction concentration of the total amount of DNA above a predetermined threshold. In preferred embodiments, an amplification of the foetal DNA sequences in the sample is carried out. Any amplification method known to the skilled person may be used, such as a PCR method.

In a preferred embodiment data from Applicant's Clarigo test that does not involve the detection of SNP (or single-nucleotide polymorphism, i.e. a genetic marker that comprises a single variable nucleotide) alleles on the foetal DNA that are not present in the DNA of the pregnant female, is used. The Clarigo test consists in targeted sequencing of a number of regions on the human genome (in other words, targeting specific genetic markers), using known SNPs (single-nucleotide polymorphism) with high (e.g. greater than 1%, preferably greater than 10%) population prevalence and two possible alleles (sc. a reference allele a.k.a. REF; and an alternative allele a.k.a. ALT). More details about the Clarigo test can be found on the Internet at multiplicom.com/product/clarigo, and in WO 2013/057568, which was filed in the name of the Applicant.

Now an exemplary embodiment of a method for estimating a gender of a foetus of a pregnant female will be discussed in detail. In a first measurement step, allele presences for a first plurality ($D_X$) of genetic markers of the X-chromosome and for a second plurality ($D_R$) of genetic markers of at least one reference chromosome, different from the X and Y chromosome, are measured in a sample of cell-free DNA from a pregnant female. Each allele presence representing the presence at a genetic marker of at least one of: a reference allele of maternal or foetal origin, and an alternative allele of maternal or foetal origin. In a second calculating step, based on said measured allele presences for said first plurality, a first fraction ($F_X$) thereof which is associated with purely homozygous genetic markers, is determined, and based on said measured allele presences for said second plurality, a second fraction ($F_R$) thereof which is associated with purely homozygous genetic markers, is determined. In a third step a gender of the foetus is estimated based on said first and second fraction. In the exemplary embodiment set out below, the estimating step comprises calculating a first gender estimator for a specific sample, calculating a second gender estimator using also data from other samples, and calculating a combined gender estimator for the specific sample based on the first and second gender estimator.

Measurement and Fraction Determining

An advantageous way to represent the results of measuring allele presences for a genetic marker, is to associate the following information to a variant data point for that genetic marker. A variant data point (being a data point associated with a number of variants, such as alleles) is used in this specification as a convenient representation for a genetic marker, and thus represents the result of measuring allele presences in a number of amplicons for genetic markers. An amplicon is a piece of DNA or RNA that is the (source and/or) product of amplification or replication events. In other words, an amplicon is a biophysical piece of replication material, designed to contain a known SNP position with high population prevalence. Each variant data point is thus associated with a known SNP with high population prevalence and with two possible alleles (sc. a reference allele a.k.a. REF; and an alternative allele a.k.a. ALT). For each variant data point $A_i$, the following numbers can be determined using e.g. a standard bioinformatics pipeline applied on the sequencing data:

The number of reads containing the REF allele on the known SNP position, $C_{Ri}$.

The number of reads containing the ALT allele on the known SNP position, $C_{Ai}$.

The total coverage $C_{Ti} = C_{Ri} + C_{Ai}$.

The allele frequency, or the fraction of ALT allele reads on the total coverage $F_i = C_{Ai}/(C_{Ri} + C_{Ai})$.

Therefore, for a given genetic marker i, the allele presences can be measured for both the REF allele, for the ALT allele, and for both alleles, by measuring the numbers of reads containing the REF allele, the ALT allele and both the REF and the ALT alleles respectively. Based on the measured allele presences, a corresponding number of allele frequencies are calculated for the predetermined number of genetic markers.

For each position in the genome (i.e. for each genetic locus), excluding the X and Y chromosomes and assuming that there are no relevant chromosome disorders, there are four copies present in the sample (assuming the position is not part of an aneuploidy region), which determine the total number of reads: two copies from the maternal DNA and two copies from the foetal DNA.

For an individual variant data point (i.e. for an individual genetic marker), let A and B denote the REF and ALT allele for the known SNP on the maternal DNA for that genetic marker, and a and b the corresponding states for the foetal DNA. This means that the variant data point can be in the possible states listed in Table 1:

TABLE 1

| variant data point state | Expected fraction ALT reads ($F_i$) |
|---|---|
| AAaa | 0 |
| AAab | FF/2 |
| ABaa | 0.5 − FF/2 ← (1 − FF)/2 |
| ABab | 0.5 |
| ABbb | 0.5 + FF/2 ← (1 − FF)/2 + FF |
| BBab | 1 − FF/2 |
| BBbb | 1 |

Figure 1:
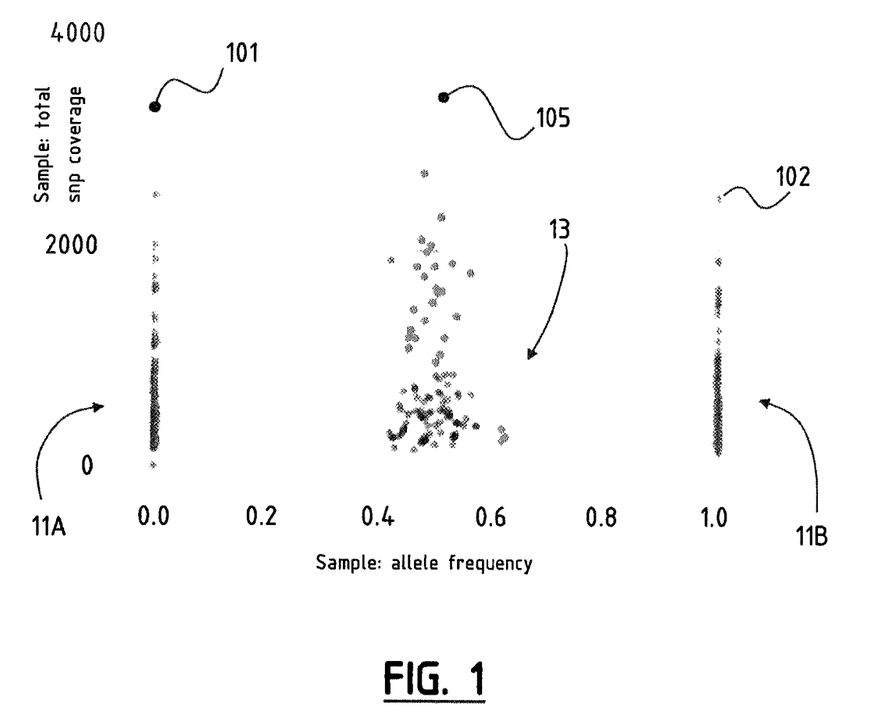
FIG. 1 is a graph showing the total SNP coverage versus allele frequency on chromosome X for sample M.
Figure 2:
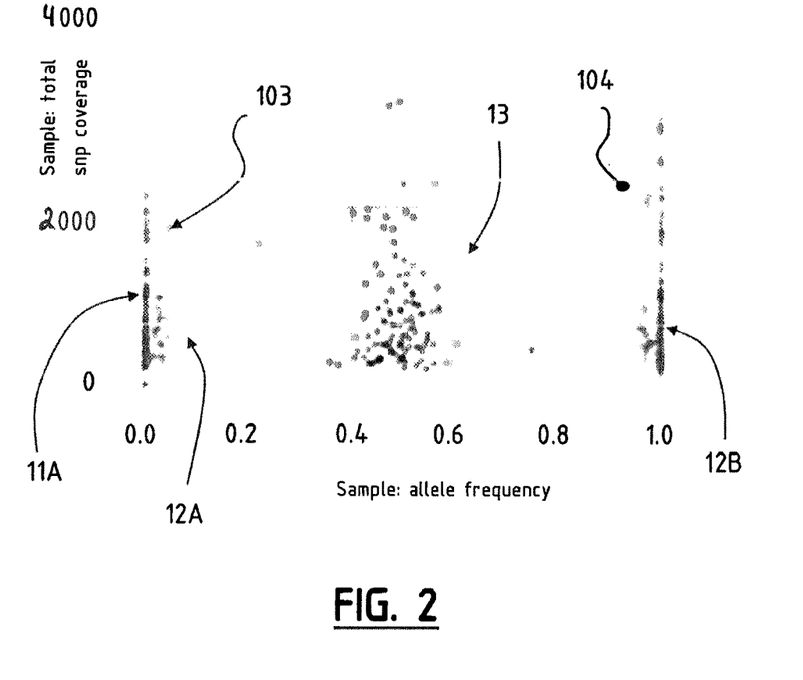
FIG. 2 is a graph showing the total SNP coverage versus allele frequency on chromosome X for sample F.

As an illustration of measured allele presences, the scatter plots illustrated in FIGS. 1 and 2 shows data for a sample M (male foetus) and a sample F (female foetus) for which allele presences for genetic markers for the X-chromosome have been measured, wherein:

Each point is a variant data point (representing the result of measurements made on amplicons) for genetic markers of the X-chromosome.

The horizontal axis shows the fraction of reads with the ALT SNP allele (i.e., the allele frequency $F_i$).

The vertical axis shows the total read coverage $C_{Ti}$.

It can be seen from FIG. 1 that specific variant data points are associated with a specific allele frequency. For example, variant data point 101 is shown on the left, and represents a genetic marker for which approximately 3300 reads were performed. All or nearly all reads for this genetic marker have measured the allele presence to indicate that REF alleles (i.e. A) are present, but not that ALT alleles are present (i.e. B). Therefore, variant data point 101 has been plotted on the left in FIG. 1, where the allele frequency is approximately 0, and likely represents a homozygous genetic marker AAaa. Variant data point 102 is shown on the right, and represents a genetic marker for which approximately 2500 reads were performed. All or nearly all reads for this genetic marker have measured the allele presence to indicate that REF alleles (i.e. A) are not present, but that ALT alleles (i.e. B) are present. Therefore, variant data point 102 has been plotted on the right in FIG. 1, where the allele frequency is approximately 1, and likely represents a homozygous genetic marker BBbb.

In FIG. 2 variant data point 103 represents a genetic marker for which approximately 1800 reads were performed. The measured allele presences allow one to calculate the allele frequency, which is relatively low, but non-zero. Therefore, variant data point 103 likely represents a genetic marker that is maternally homozygous for the reference allele pair but has a heterozygous allele pair of foetal origin (thus AAab), since the fraction of maternal DNA present in the sample for the genetic marker is (much) greater than the fraction of foetal DNA present in the sample for the genetic marker. Variant data point 104 is shown on the right, and represents a genetic marker for which approximately 2250 reads were performed. By the same reasoning, variant data point 104 likely represents a genetic marker that is maternally homozygous for the alternative allele pair but has a heterozygous allele pair of foetal origin (thus BBab).

In FIG. 1 variant data point 105 represents a genetic marker for which approximately 2750 reads were performed. The measured allele presences allow one to calculate the allele frequency, which is found to be approximately 0.48. Therefore, variant data point 105 likely represents a genetic marker that is maternally heterozygous (thus AB).

Therefore, three groups of variant data points (11A and 11B, 12A and 12B, and 13) can be distinguished:
  variant data points 11A and 11B that are homozygous in the maternal and foetal DNA (AAaa, BBbb);
  variant data points 12A and 12B that are homozygous in the maternal DNA, and heterozygous in the foetal DNA (AAab, BBab). Note that in these cases the foetal DNA contains an allele that was inherited from the father and that is not present in the maternal DNA. In other words, for a male foetus this group of variant data points will not be present for the X-chromosome, see FIG. 1;
  variant data points 13 that are heterozygous in the maternal DNA (ABaa, ABab, bb).

It is noted that multiple variant data points may have the same (or very nearly the same) allele frequency, especially when they are part of the same group. This means that (very nearly) the same number of allele presences has been measured for them, relatively to the total number of reads.

It is also noted that, in FIGS. 1 and 2, variant data points with a higher total read coverage (closer to the top of the plot) have a more accurate allele frequency, simply since there are more measurement data. This property may be taken into account when determining a statistical reliability for a given variant data point.

Homozygous Fraction Gender Estimator (First Gender Estimator)

A first gender estimator is calculated by investigating the fraction of variant data points that are purely homozygous in the sample for the X-chromosome and for the at least one reference chromosome which does not include the X/Y-chromosome. In a preferred embodiment all reference chromosomes may be used.

The following parameters are calculated from the obtained measurement results:
  the total number $D_X$ of reads over all variant data points on chromosome X, i.e. the total number of measured allele presences for the first plurality of genetic markers of the chromosome X;
  the total number $D_{Xh}$ of reads on chromosome X, corresponding to variant data points that are purely homozygous, i.e. allele frequency either 0 or 1, within a predetermined error margin, i.e. groups 11A and 11B in FIGS. 1 and 2;

the total number $D_R$ of reads over all variant data points on the at least one reference chromosome (this may be all chromosomes excluding the X-chromosome and the Y-chromosome); i.e. the total number of measured allele presences for the second plurality of genetic markers of the at least one reference chromosome;

the total number $D_{Rh}$ of reads on the at least one reference chromosome, corresponding to variant data points that are purely homozygous, i.e. an allele frequency which is either 0 or 1, within a predetermined error margin;

For sample M, the following set of values is obtained by the method (see FIG. 1 for the variant data points on the X-chromosome):

$D_X$=227542 (divided among 390 amplicons), $D_{Xh}$=162151 (divided among a subset of 285 amplicons), $D_R$=883695 (divided among 1681 amplicons), $D_{Rh}$=491752 (divided among a subset of 917 amplicons).

For sample F, the following set of values are identified by the method (see FIG. 2 for the variant data points on the X-chromosome):

$D_R$=942355 (divided among 1680 amplicons), $D_{Rh}$=541801 (divided among a subset of 953 amplicons), $D_X$=255394 (divided among 391 amplicons), $D_{Xh}$=143376 (divided among a subset of 228 amplicons).

Next, the following fractions are calculated:

a first fraction $F_X$ of reads for the first plurality of genetic markers, which is associated with purely homozygous genetic markers:

$$F_X = D_{Xh}/D_X,$$

a second fraction $F_R$ of reads for the second plurality of genetic markers, which is associated with purely homozygous genetic markers:

$$F_R = D_{Rh}/D_R.$$

A first preliminary gender estimator may be calculated as:

$$E_{H0} = F_X/F_R.$$

In case of a female foetus, there are two copies present of chromosome X and of the at least one reference chromosome. Hence, $E_{H0}$ is expected to be 1. In case of a male foetus, there is only one copy of chromosome X, but two copies of all reference chromosomes. Hence, $E_{H0}$ is expected to be larger than 1. In other words, the first preliminary gender estimator allows to estimate the gender.

For the exemplary embodiment of FIG. 1 (sample M), the fractions that are purely homozygous and the preliminary gender estimator $E_{H0}$ can be calculated as:

$$F_X = D_{Xh}/D_X \cong 0.71,$$

$$F_R = D_{Rh}/D_R \cong 0.55,$$

$$E_{H0} = F_X/F_R \cong 1.28.$$

Because $E_{H0}$ is well above 1, sample M can be estimated to be male.

For the exemplary embodiment of FIG. 2 (sample F), the fractions that are purely homozygous and the preliminary gender estimator $E_{H0}$ can be calculated as:

$$F_X = D_{Xh}/D_X \cong 0.56,$$

$$F_R = D_{Rh}/D_R \cong 0.57,$$

$$E_{H0} = F_X/F_R \cong 0.97.$$

Because $E_{H0}$ is approximately 1, sample F can be estimated to be female.

This can be further understood as follows. Given two copies of chromosome X, REF allele A and ALT allele B, there are four different combinations of those alleles possible for the mother that are expected to appear: AA, AB, BA, BB. Based on the gender of the foetus, the above combinations can be further divided due to the presence of foetal DNA:

1. Male foetus (FIG. 1, sample M): the DNA content on chromosome X consists of two copies from the mother and a single copy of the foetus inherited from the mother, in an amount equal to half the foetal fraction. The following allele combinations can be distinguished:
   a. AAa, BBb: purely homozygous.
   b. ABa, ABb, BAa, BAb: heterozygous.
2. Female foetus (FIG. 2, sample F): the DNA content on chromosome X consists of two copies from the mother and two copies from the foetus, one of which is inherited from the mother and another inherited from the father, with an amount equal to the foetal fraction. The following groups can be distinguished:
   a. AAaa, BBbb: purely homozygous.
   b. AAab, BBab: homozygous allele pairs of maternal origin and heterozygous allele pairs of foetal origin.
   c. ABaa, ABab, ABba, ABbb, BAaa, BAab, BAba, BAbb: heterozygous allele pairs of maternal origin.

From the above, it follows that the expected first fraction of purely homozygous SNPs on the X-chromosomes should be higher in case of a male foetus compared to a female foetus. For a female foetus, this first fraction is expected to be identical to the second fraction obtained from non-sex chromosomes. For a male foetus, the first fraction is expected to be higher than the second fraction.

The first preliminary gender estimator $E_{H0}$ may be standardised to a first gender estimator $E_{H1}$ which is expected to be 0 for a female foetus, and 1 for male foetus:

$$E_{H1} = (E_{H0}-1)/(E_{He}-1).$$

with $E_{He}$ a predicted value for $E_{H0}$ in case of a male foetus.

This predicted value $E_{He}$ may be obtained by estimating the population SNP heterozygosity level using the fraction of SNPs that is observed as heterozygous in the mother's DNA in the sample. This estimating can be done as follows. The following definitions are introduced:

the total number $D_{Rhet}$ of reads on the at least one reference chromosome, corresponding to variant data points that are heterozygous in the maternal DNA. For the heterozygous variant data points, there are 8 possibilities: ABaa, ABbb, ABab, ABba, BAaa, BAbb, BAab and BAba.

The fraction of heterozygous variant data points for the at least one reference chromosome can then be calculated as:

$$F_{Rhet} = D_{Rhet}/D_R.$$

This can be further understood as follows. Suppose on average, the REF allele A can be found in a fraction $F_A$ of all occurrences of an SNP and the ALT allele in a fraction $F_B = 1 - F_A$. If a generalization is made that states that every SNP in the variant data points shares the same REF allele fraction $F_A$, expected levels of homozygosity and heterozygosity can be estimated. The level of homozygosity, or equivalently, the level of occurrence of the combinations AA, BB is estimated by:

$$F_A^2 + F_B^2 = F_A^2 + (1-F_A)^2.$$

The level of heterozygosity, or equivalently, the level of occurrence of the combinations AB, BA is $$F_{Rhet} = 2 F_A F_B = 2 F_A (1-F_A).$$

The combinations AAa, BBb have the same level of occurrence as the combinations AA, BB.

The occurrence of the combinations AAaa, BBbb is $F_A^3 + F_B^3 = F_A^3 + (1-F_A)^3$.

The occurrence of the other combinations can be estimated in a similar way.

From the above, it follows that a predicted value for $E_{H0}$ in case of a male foetus can be estimated as:

$$E_{He} = F_A^2 + (1-F_A)^2/F_A^3 + (1-F_A)^3.$$

The method estimates the value $F_A$ from the observed level of heterozygosity on the at least one reference chromosome $F_{Rhet}$ by solving the following second order degree equation and taking the largest root:

$$2F_A(1-F_A) - F_{Rhet} = 0.$$

If no real root exists, $F_A$ is set to 0.5.

A first gender classification may be executed based on $E_{H1}$, using a fixed threshold $T_0 (\leq 0.5)$:

$$E_{H1} < T_0: \text{female,}$$

$$E_{H1} \geq T_0 \text{ and } E_{H1} \leq 1-T_0: \text{unknown,}$$

$$E_{H1} > 1-T_0: \text{male.}$$

For sample M, the first gender estimator can be calculated as follows. First $D_{Rhet}$ is determined: $D_{Rhet} = 259134$ (divided among 498 amplicons), and next the fraction is calculated:

$$F_{Rhet} = D_{Rhet}/D_R \cong 0.29.$$

From this fraction the predicted value $E_{He}$ can be calculated:

$$F_A \cong 0.82,$$

$$E_{He} \cong 1.25.$$

The first gender estimator then becomes:

$$E_{H1} = (E_{H0}-1)/(E_{He}-1) \cong 1.07.$$

Based on this value, a first classification of sample M is male.

For sample F, the first gender estimator can be calculated as follows. First $D_{Rhet}$ is determined: $D_{Rhet} = 250259$ (divided among 436 amplicons), and next the fraction is calculated:

$$F_{Rhet} = D_{Rhet}/D_R \cong 0.26.$$

From this fraction the predicted value $E_{He}$ can be calculated:

$$F_A \cong 0.84,$$

$$E_{He} \cong 1.25.$$

The first gender estimator then becomes:

$$E_{H1} = (E_{H0}-1)/(E_{He}-1) \cong -0.10.$$

Based on this value, a first classification of sample F is female.

Figure 3:
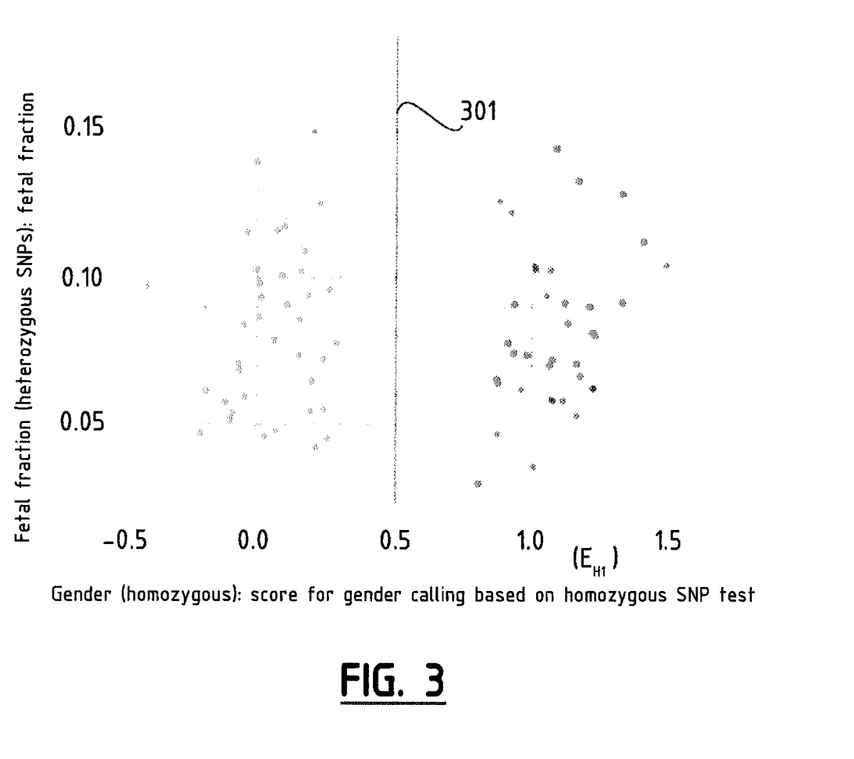
FIG. 3 is a graph plotting for a set of samples the gender estimator $E_{H1}$ on the X-axis versus the foetal fraction on the Y-axis.

FIG. 3 illustrates a first gender estimator $E_{H1}$ (X-axis) for a batch of samples with different foetal fractions (Y axis). The samples (each point represents a sample) on the left of the vertical line 301 correspond with a first estimator indicating a female foetus, and the samples on the right of the vertical line 301 correspond with a first estimator indicating a male foetus.

Coverage Gender Estimator (Second Gender Estimator)

A second gender estimator is obtained by comparing the coverage of the X-chromosome to the coverage of a set of at least one reference chromosome different from the X and Y chromosomes. This set may be the same set as the set used for determining the first gender estimator, or a different set.

The following parameters are calculated from the variant data points of a sample i of a batch:

the total number $D_{Xi}$ of reads over all variant data points on chromosome X, i.e. the total number of measured allele presences for the first plurality of genetic markers of the X-chromosome; and the total number of reads $D_{Ri}$ over all variant data points on the at least one reference chromosome, i.e. the total number of measured allele presences for the second plurality of genetic markers of the at least one reference chromosome.

Next, a ratio $N_{Xi}$ of the reads $D_{Xi}$ and the reads $D_{Ri}$ is calculated as follows for sample i:

$$N_{Xi} = D_{Xi}/D_{Ri}.$$

The ratio $N_{Xi}$ may be calculated for all samples in an analysis batch, e.g. all samples sequenced during a single run. Next, the values $N_{Xi}$ for the samples that were determined "female" using the first gender classification may be selected, and there may be calculated normal distribution parameters for those values, e.g. a mean value $\mu$ and standard deviation $\sigma$.

In the event that the number of samples in the analysis batch that were classified "female" is too small to obtain a reliable estimate of the distribution, this set can be augmented by using samples classified as "male", using a corrected value:

$$N'_{Xi} = N_{Xi} \times 1/(1-FF/2).$$

with FF the estimated foetal fraction of the sample. The foetal fraction may be estimated using an embodiment of the method disclosed in patent application BE 2015/5460 in the name of the Applicant which is included herein by reference. Other existing methods may also be used to estimate the foetal fraction.

Using this distribution, a z-score $Z_{Oi}$ can be calculated for all samples i in the analysis batch:

$$Z_{Oi} = \frac{N_{Xi} - \mu}{\sigma}.$$

For each sample, determine $Z_{Mi}$, the expected z-score value under the assumption that the sample is "male". This value is based on the estimated foetal fraction of the sample:

$$Z_{Mi} = -\frac{\mu}{\sigma} \times \frac{FF}{2}.$$

A second gender estimator is calculated as:

$$E_{H2} = Z_{Oi}/Z_{Mi}.$$

This value is expected to be 0 for a female foetus, and 1 for a male foetus.

For samples M and F the ratio $N_{Xi}$ can be calculated using the formulas above:

$$N_{XM} = 0.1225806583663057,$$

$$N_{XF} = 0.12775398163696797.$$

Figure 4:
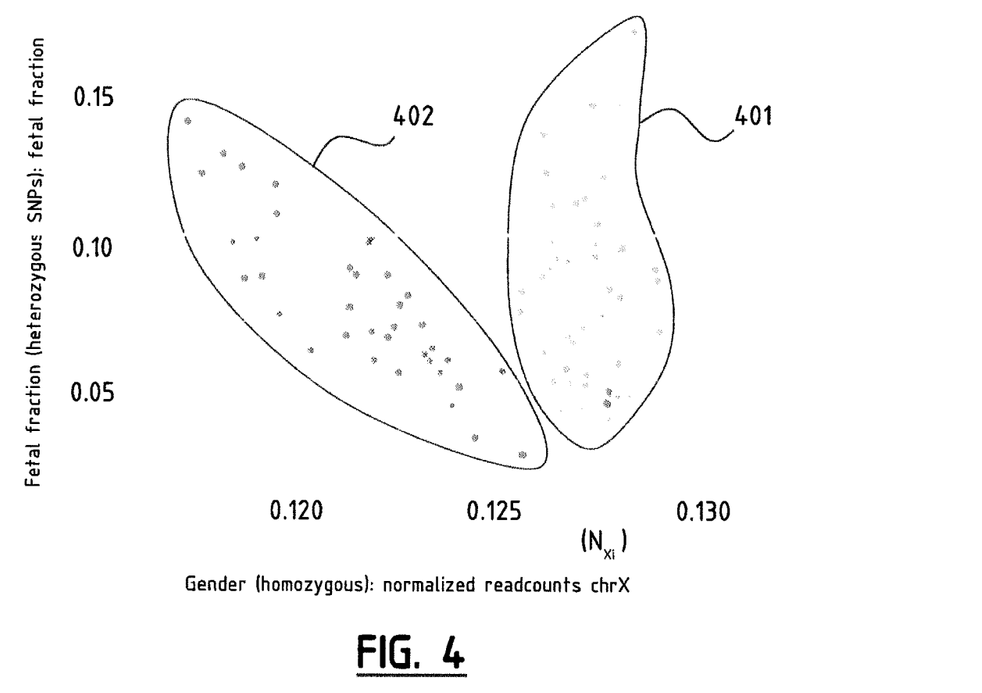
FIG. 4 is a graph plotting for the set of samples of FIG. 3, the ratio $N_{Xi}$ on the X-axis versus the foetal fraction on the Y-axis.

Next all values $N_{Xi}$ are calculated for all samples in the analysis batch. FIG. 4 shows the values $N_{Xi}$ for all samples in function of their foetal fraction FF. The samples classified as female by the first gender estimator $E_{H1}$ are shown in a contour 401 and the samples preliminarily classified as male are shown in a contour 402.

The samples classified as female (i.e. the points in contour 401) are used to determine a normal distribution. These are the samples for which $E_{H1} < T_0$. These samples can be found on the left of the vertical separation line 301 in FIG. 3.

In the example of FIGS. 3 and 4, there are enough female samples to accurately estimate the normal distribution. If this would not have been the case, values $N'_{Xi}$ may be used for male samples to estimate the distribution. For sample M (with FF=5.8%), this would mean:

$$N'_{XM} = N_{XM} \times 1/(1-FF/2) = 0.12626348981879823.$$

Figure 5:
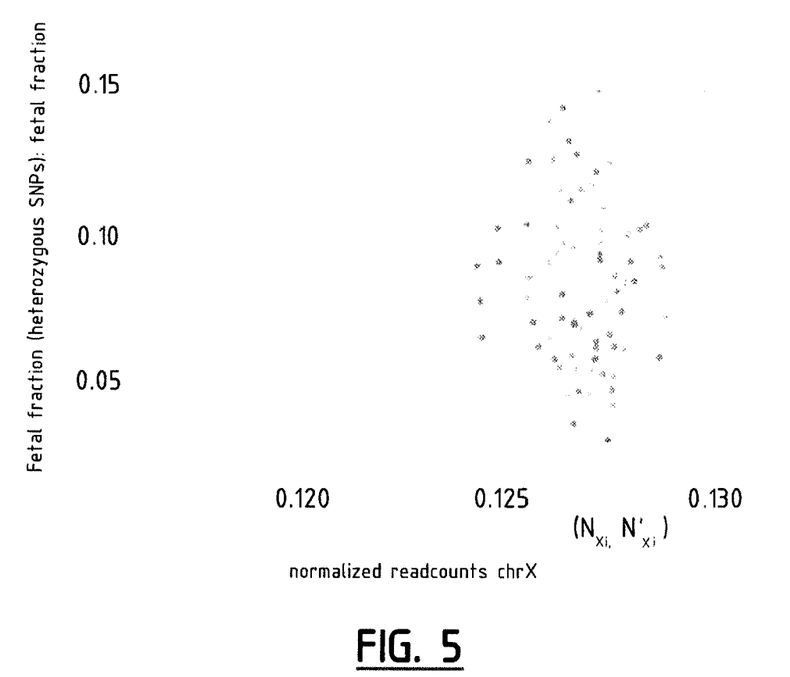
FIG. 5 is a graph plotting for the set of samples of FIG. 3, the ratio $N_{Xi}$ for samples classified as female (according to $E_{H1}$), and $N'_{Xi}$ for samples classified as male (according to $E_{H1}$) on the X-axis versus the foetal fraction on the Y-axis.

FIG. 5 shows the effect of normalizing values $N_{Xi}$ to $N'_{Xi}$ for samples classified male by the first gender estimator.

Based on the values $N_{Xi}$, the normal distribution is calculated with:

mean value μ=0.12792346387904036, and standard deviation σ=0.0011732807075874412.

Figure 6:
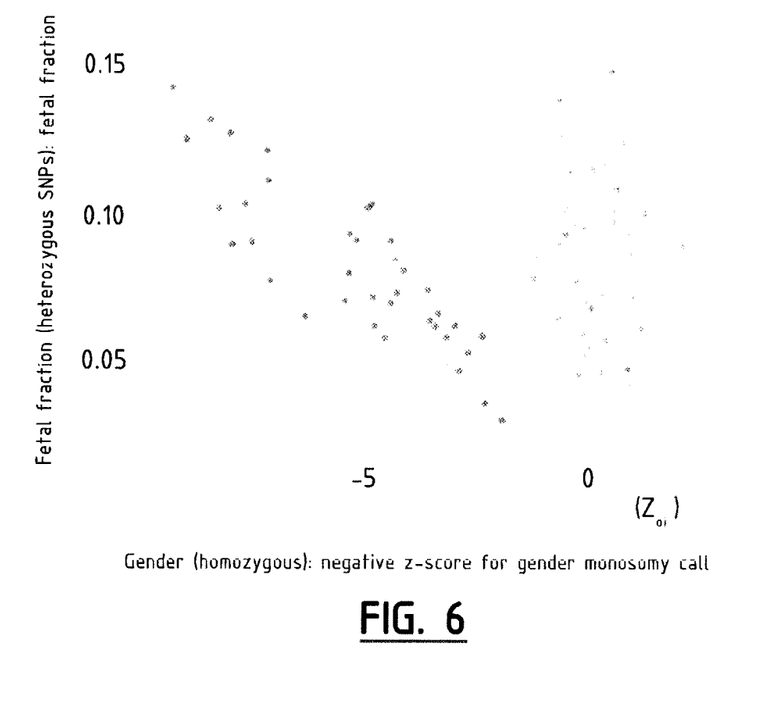
FIG. 6 is a graph plotting for the set of samples of FIG. 3, the z-score $Z_{Oi}$ on the X-axis versus the foetal fraction on the Y-axis.

Using this distribution, a z-score $Z_{OM} = -4.55$ for sample M and $Z_{OF} = -0.14$ for sample F are calculated. The z-score for all samples in the analysis batch is shown in FIG. 6.

The expected z-score value under the assumption that the sample is "male" for the two example samples are $Z_{MM} = -3.18$ and $Z_{MF} = -2.84$. Using both z-scores, the second gender estimation of samples M and F are:

Sample M: $E_{H2} = Z_{OM}/Z_{MM} = 1.43$,

Sample F: $E_{H2} = Z_{OF}/Z_{MF} = 0.05$.

Figure 7:
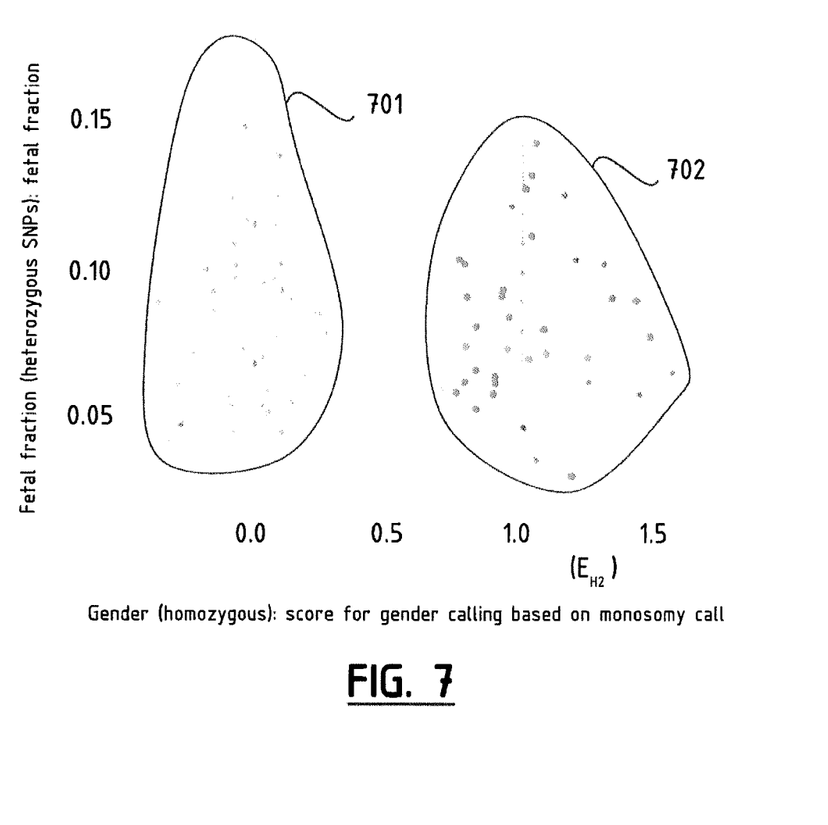
FIG. 7 is a graph plotting for the set of samples of FIG. 3 the second gender estimator $E_{H2}$ on the X-axis versus the foetal fraction on the Y-axis.

The second gender estimator values for all samples in the analysis batch are shown on the x-axis of FIG. 7. Samples classified female are shown in a contour 701 and samples classified as male are shown in a contour 702.

Combined Gender Estimator

Both the first and the second gender estimators may be combined into a single joint estimator.

In case of a female foetus, the combined estimator pair is expected to have the following values:

$(E_{H1}, E_{H2}) = (0,0)$.

In case of a male foetus, the combined estimator pair is expected to have the following values:

$(E_{H1}, E_{H2}) = (1,1)$.

For a specific sample, the Euclidian distances between the observed estimator value pairs and both expected value pairs may be calculated:

$D_F = \sqrt{E_{H1}^2 + E_{H2}^2}$ $D_M = \sqrt{(E_{H1}-1)^2 + (E_{H2}-1)^2}$

From this, a single combined estimator is calculated as $E_H = (D_M - D_F)/\sqrt{2}$.

This value is expected to be −1 for a male foetus, and +1 for a female foetus.

Using the final gender estimator, a final estimation may be performed as follows, using a predetermined threshold T (≥0):

$E_H < -T$: male, $E_H \geq -T$ and $E_H \leq +T$: unknown, $E_H > +T$: female.

Figure 8:
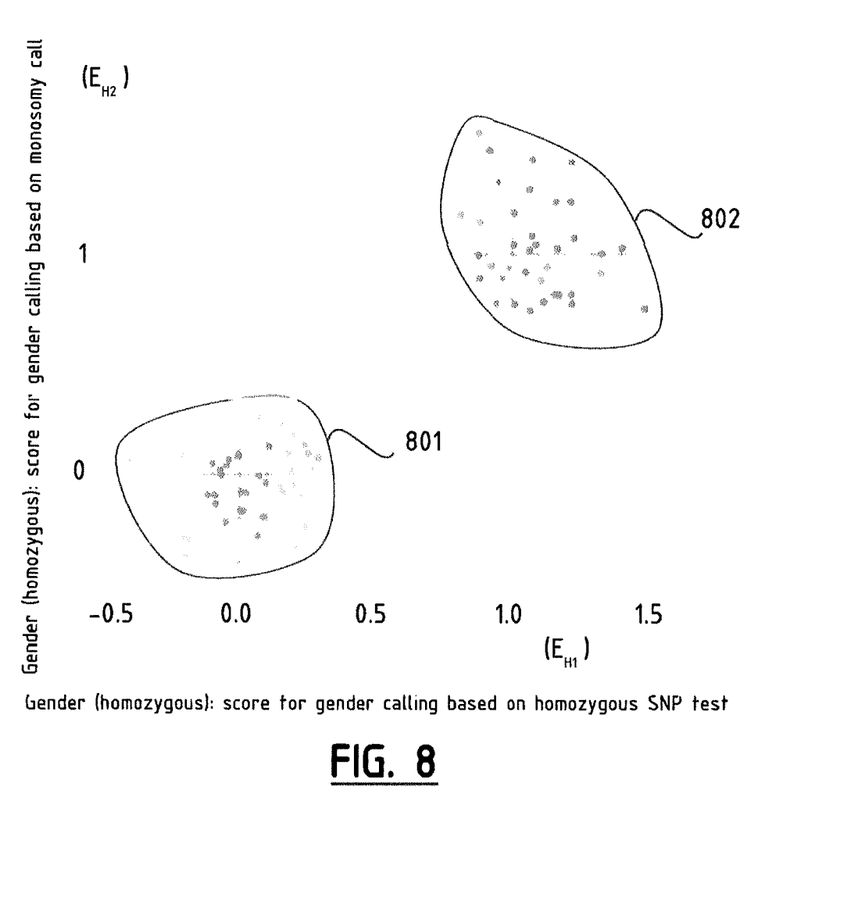
FIG. 8 is a graph plotting for the set of samples of FIG. 3 the first gender estimator $E_{H1}$ on the X-axis versus the second gender estimator $E_{H2}$ on the Y-axis.

The gender estimators resulted in values (1.07, 1.43) for sample M and values (−0.10, 0.05) for sample F. FIG. 8 shows the values of both estimators for all samples in the analysis batch. Samples whose estimator values are centred around (0,0) will be classified as female and are shown in a contour 801. Samples whose estimator values are centred around (1,1) will be classified as male and are shown in a contour 802.

Finally, a combined estimator value for samples M and F can be calculated:

Sample M: $E_H = -0.95$,

Sample F: $E_H = 0.94$.

Figure 9:
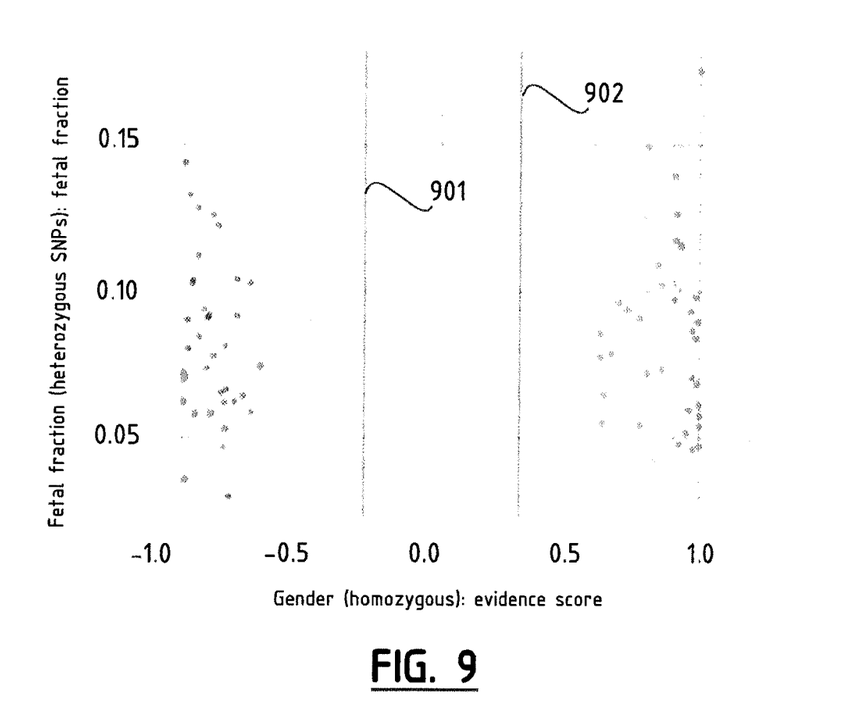
FIG. 9 is a graph plotting for the set of samples of FIG. 3 the combined gender estimator $E_H$ on the X-axis versus the foetal fraction on the Y-axis.

Based on these values and threshold T=0.3, sample M is classified as male and sample F is classified as female. The value of $E_H$ for all samples in the example analysis batch is shown in FIG. 9. Samples classified as female are shown on the left side of vertical line 901, and samples classified as male are shown on the right side of vertical line 902. Any sample points between lines 901 and 902 (none were present in the present example) would be classified as unknown. The threshold value T was determined empirically using a large data set.

Figure 10:
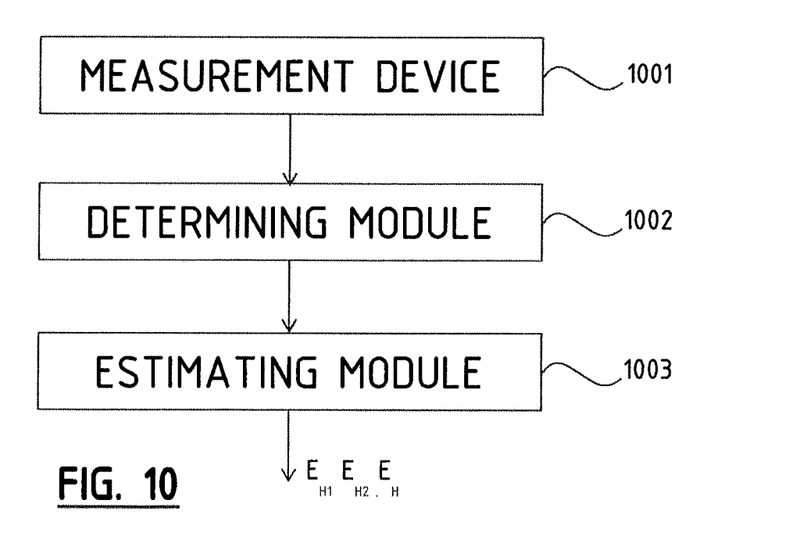
FIG. 10 is a schematic drawing of an embodiment of a system.

FIG. 10 illustrates an embodiment of a system of the invention for estimating a gender of a foetus of a pregnant female. The system comprises a measurement device 1001, a determination module 1002, and an estimating module 1003. The measurement device 1001 is configured for measuring allele presences ($D_X$) for a first plurality of genetic markers of the X-chromosome and allele presences ($D_R$) for a second plurality of genetic markers of at least one reference chromosome, different from the X and Y chromosome, in a sample of cell-free DNA from a pregnant female. The determination module 1002 is configured for determining a first fraction ($F_X$) of said measured allele presences for said first plurality which is associated with purely homozygous genetic markers, and a second fraction ($F_R$) of said measured allele presences for said second plurality which is associated with purely homozygous genetic markers. The estimation module 1003 is configured for estimating a gender of said foetus based on said first and second fraction. The estimating may be done according to any one of the above described exemplary embodiments.

A person of skill in the art would readily recognize that steps of various above-described methods can be performed by programmed computers. Herein, some embodiments are also intended to cover program storage devices, e.g., digital data storage media, which are machine or computer readable and encode machine-executable or computer-executable programs of instructions, wherein said instructions perform some or all of the steps of said above-described methods. The program storage devices may be, e.g., digital memories, magnetic storage media such as a magnetic disks and magnetic tapes, hard drives, or optically readable digital data storage media. The embodiments are also intended to cover computers programmed to perform said steps of the above-described methods.

The functions of the various elements shown in the figures, including any functional blocks labelled as "modules", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "module" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included.

Whilst the principles of the invention have been set out above in connection with specific embodiments, it is to be understood that this description is merely made by way of example and not as a limitation of the scope of protection which is determined by the appended claims

The invention claimed is:

1. A method for estimating a gender of a fetus of a pregnant female, said method comprising the following steps:
measuring allele presences ($D_X$) for a first plurality of genetic markers of the X-chromosome and allele presences ($D_R$) for a second plurality of genetic markers of at least one reference chromosome, different from the X and Y chromosome, in a sample of cell-free DNA from a pregnant female; each allele presence representing the presence at a genetic marker of at least one of: a reference allele of maternal or fetal origin or an alternative allele of maternal or fetal origin;
determining, by a computer device, a first fraction ($F_X$) thereof which is associated with purely homozygous genetic markers based on said measured allele presences for said first plurality;
determining, by the computer device, a second fraction ($F_R$) thereof which is associated with purely homozygous genetic markers based on said measured allele presences for said second plurality;
determining, by the computer device, a first gender estimator ($E_{H1}$) based on said first and second fractions;
determining, by the computer device, a ratio ($N_{Xi}$) between the measured allele presences of the first plurality and the measured allele presences of the second plurality of genetic markers, and determining statistical distribution parameters of the ratio associated with a first gender estimator which indicates that the fetus is female, and
determining, by the computer device, a second gender estimator ($E_{H2}$) using the statistical distribution; and
estimating, by the computer device, a gender of said fetus, using the first and second gender estimator;
wherein the first gender estimator ($E_{H1}$), is calculated as follows:

$$E_{H1}=(E_{H0}-1)/(E_{He}-1),$$

with $E_{H0}=F_X/F_R$;
with $F_X$ the first fraction;
with $F_R$ the second fraction; and
with $E_{He}$ a predicted value for $E_{H0}$ in case of a male fetus, and
wherein $E_{H1}$ is approximately 0 for a female fetus, and approximately 1 for male fetus.

2. The method of claim 1, wherein the determining of the first fraction comprises:

calculating a corresponding number of allele frequencies for said first plurality based on said measured allele presences for the first plurality of genetic markers; and
determining as the first fraction the fraction of said measured allele presences for which the allele frequency is 0 or 1 within a predetermined error margin; and/or
wherein the determining of the second fraction comprises:
calculating a corresponding number of allele frequencies for said second plurality based on said measured allele presences for the second plurality of genetic markers; and
determining as the second fraction the fraction of said measured allele presences for which the allele frequency is 0 or 1 within a predetermined error margin.

3. The method of claim 1,
wherein the measuring and determining steps are performed, by the computer device, for a batch comprising a plurality of samples; wherein for each sample in the batch, the first and second fraction are calculated.

4. The method of claim 1, wherein the second gender estimator $E_{H2}$ is calculated as follows $$E_{H2}=Z_{Oi}/Z_{Mi},$$

with $Z_{Oi}$ a z-score calculated for the sample i in an analysis batch as:

$$Z_{Oi} = \frac{N_{Xi} - \mu}{\sigma}$$

with $Z_{Mi}$, an expected z-score value under the assumption that the sample i is "male":

$$Z_{Mi} = \frac{\mu}{\sigma} \times \frac{FF}{2}$$

with FF a calculated fetal fraction of sample i,
with $\mu$ a mean value and $\sigma$ a standard deviation calculated for values $N_{Xi}$ for a plurality of samples of a batch that were determined "female" using the first gender estimator,
with $N_{Xi}$ a ratio between measured allele presences of a first plurality of genetic markers of the X-chromosome and measured allele presences of a second plurality of genetic markers of a reference chromosome, for a sample i.

5. The method of claim 1, wherein the sample is obtained from maternal blood, plasma, urine, cerebrospinal fluid, serum, saliva or is transcervical lavage fluid.

6. The method of claim 1, wherein said measuring step comprises at least one of the following: polymerase chain reaction (PCR), ligase chain reaction, nucleic acid sequence based amplification (NASBA), and/or branched DNA methods.

7. The method of claim 6, wherein said measuring step comprises PCR.

* * * * *